US00RE34196E

United States Patent [19]

Munro

[11] E Patent Number: Re. 34,196

[45] Reissued Date of Patent: Mar. 16, 1993

[54] METHOD AND MATERIAL FOR BRIGHTENING TEETH

[75] Inventor: John R. Munro, Knoxville, Tenn.

[73] Assignee: Dunhall Pharmaceuticals, Inc., Gravette, Ark.

[21] Appl. No.: 743,611

[22] Filed: Aug. 7, 1991

Related U.S. Patent Documents

Reissue of:

[64] Patent No.: 4,990,089
Issued: Feb. 5, 1991
Appl. No.: 519,318
Filed: May 4, 1990

U.S. Applications:

[63] Continuation of Ser. No. 235,304, Aug. 23, 1988, abandoned.

[51] Int. Cl.[5] ..... A61C 5/00

[52] U.S. Cl. ..... 433/215; 433/80; 424/53

[58] Field of Search ..... 433/80, 203.1, 215, 433/216, 229, 6, 48; 128/861, 862; 424/616, 56, 53, 70

[56] References Cited

U.S. PATENT DOCUMENTS

| | | | |
|---|---|---|---|
| Re. 28,667 | 12/1975 | Gores . | |
| 165,584 | 7/1875 | Hopfen . | |
| 767,553 | 8/1904 | Edgelow . | |
| 803,474 | 10/1905 | Dennis . | |
| 803,475 | 10/1905 | Dennis . | |
| 1,371,029 | 3/1921 | Jennings . | |
| 1,818,146 | 8/1931 | Maker . | |
| 1,934,688 | 11/1933 | Ackerman | 32/5 |
| 2,152,391 | 3/1939 | Spahn | 32/34 |
| 2,257,709 | 9/1941 | Anderson | 128/260 |
| 2,669,988 | 2/1954 | Carpenter | 128/136 |
| 2,835,628 | 5/1958 | Saffir | 167/84 |
| 2,884,925 | 5/1959 | Meynier, Jr. | 128/270 |
| 3,060,935 | 10/1962 | Riddell | 128/260 |
| 3,073,300 | 1/1963 | Berghash | 128/136 |
| 3,107,668 | 10/1963 | Thompson | 128/861 |
| 3,247,844 | 4/1966 | Berghash | 128/136 |
| 3,379,193 | 4/1968 | Monaghan | 128/136 |
| 3,416,527 | 12/1968 | Hoef | 128/260 |
| 3,448,738 | 6/1969 | Berghash | 128/136 |
| 3,481,329 | 12/1969 | Warren, Jr. | 128/66 |
| 3,505,995 | 4/1970 | Greenberg | 128/136 |
| 3,527,218 | 9/1970 | Westline | 128/229 |
| 3,527,219 | 9/1970 | Greenberg | 128/260 |
| 3,536,069 | 10/1970 | Gores | 128/136 |
| 3,567,823 | 3/1971 | Yamaga et al. | 424/132 |
| 3,624,909 | 12/1971 | Greenberg | 32/40 |
| 3,625,215 | 12/1971 | Quisling | 128/260 |
| 3,657,413 | 4/1972 | Rosenthal | 424/81 |
| 3,688,406 | 12/1972 | Porter et al. | 32/40 R |
| 3,844,286 | 10/1974 | Cowen | 128/260 |
| 3,955,281 | 5/1976 | Weitzman | 32/14 B |
| 3,988,433 | 10/1976 | Benedict | 424/53 |
| 3,998,945 | 12/1976 | Vit | 424/53 |
| 4,064,628 | 12/1977 | Weitzman | 32/14 B |
| 4,138,814 | 2/1979 | Weitzman | 32/14 B |

(List continued on next page.)

OTHER PUBLICATIONS

TP Laboratories, Inc. brochure, p. 3 (1974).

(List continued on next page.)

*Primary Examiner*—Cary E. O'Connor
*Attorney, Agent, or Firm*—Robert Hardy Falk; Tom R. Vestal; John P. Pinkerton

[57] ABSTRACT

There is disclosed a *novel* process and a [material] *composition* for brightening teeth, *together with a novel use of old compositions for brightening teeth.* The *novel* process *and use each comprises* [comprises] the [construction] *placing* of a splint around the tooth or teeth to be brightened, [followed by the insertion within the splint of] *with* a brightening agent [selected from one of many peroxide groups] *comprising a composition capable of sustained nascent oxygen release.* The splint is constructed so that the splint is relatively liquid tight [to the gingiva]. *Preferably,* the brightening agent is periodically renewed *during the day* and can be mixed with various other agents to increase the nascent oxygen release [aerating factors]. In one embodiment, the [perioxide] *peroxide* that is used is a 10% solution of carbamide peroxide mixed with a water free gel.

59 Claims, 2 Drawing Sheets

U.S. PATENT DOCUMENTS

| | | | |
|---|---|---|---|
| 4,164,940 | 8/1979 | Quinby | 128/62 A |
| 4,173,505 | 11/1979 | Jacobs | 156/285 |
| 4,302,441 | 11/1981 | Muhlemann et al. | 424/48 |
| 4,376,628 | 3/1983 | Aardse | 433/80 |
| 4,419,992 | 12/1983 | Chorbajian | 128/136 |
| 4,428,373 | 1/1984 | Seid et al. | 604/77 |
| 4,431,631 | 2/1984 | Clipper et al. | 424/53 |
| 4,519,386 | 5/1985 | Sullivan | 128/136 |
| 4,522,805 | 6/1985 | Gordon | 424/52 |
| 4,537,778 | 8/1985 | Clipper et al. | 424/53 |
| 4,544,354 | 10/1985 | Gores et al. | 433/42 |
| 4,557,692 | 10/1985 | Chorbajian | 433/215 |
| 4,560,351 | 12/1985 | Osborne | 433/80 |
| 4,592,487 | 6/1986 | Simon et al. | 222/94 |
| 4,592,588 | 6/1986 | Simon et al. | 222/94 |
| 4,685,883 | 8/1987 | Jernberg | 433/215 |
| 4,696,757 | 9/1987 | Blank et al. | 252/186.29 |
| 4,770,634 | 9/1988 | Pellico | 433/217.1 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |
| 4,983,381 | 1/1991 | Zaragoza | 424/53 |

OTHER PUBLICATIONS

Richard M. Zillich, "Bleaching Tetracycline Stains", 466 The Compendium of Continuing Education, Art. #2, vol. V, No. 6 (Jun., 1984).

Van B. Haywood, Harold O. Heymann, "Nightguard Vital Bleaching", Quintessence International, vol. 20, No. 3 at 173-176 (1989).

Maury H. Krystel, D.D.S. and John Munro, D.D.S., "Clinical Evaluation by Omni White & Brite System", Dentistry Today (1989).

John R. Munro, "Vital Bleaching Using the White & Brite System, Esthetic Dentistry Update, American Academy of Cosmetic Dentistry, vol. 1, No. 3 (Aug. 1990).

David K. Yarborough, "The Safety and Efficacy of Tooth Bleaching: Review of the Literature 1988-1990", Compend. Contin. Educ. Dent., vol. XII, No. 3.

Goldstein R. E., "Bleaching Teeth: new materials—new role", J. Am. Dent. Assoc. 115 (special issue) at 44E-52E (1987).

Nathanson D., Parra C., "Bleaching Vital Teeth: A Review and Clinical Study", Compend. Cont. Educ. Dent., 8 at 490-498 (1987).

Cohen S., Parkins F. M., "Bleaching Tetracycline-Strained Vital Teeth", Oral Surg., Oral Med., Oral Pathol., 29 at 465-471 (1970).

Arens D. E., Rich J. J., Healey J. J., "A Practical Method of Bleaching Tetracycline-Strained Teeth", Oral Surg., Oral Med., Oral Pathol., 34 at 812-817 (1972).

Kennedy N., "The Tetracycline Dilemma and Vital Bleaching Technique", Chicago Dent. Soc. Rev., 69 at 28-30 (1976).

Reid J. S., Newman P., "A Suggested Method of Bleaching Tetracycline-Strained Vital Teeth", Br. Dent. J., 5(4) at 129 (1977).

Compton D. E., "Bleaching of Tetracycline-Stained Vital Teeth:, J. Endondon., 5(4) at 129 (1979).

Christensen G. J., "Bleaching Vital Tetracycline Stained Teeth", Quintessence Int., 9(6) at 13-19 (1978).

Jordan R. E., Boksman L., "Conservative Vital Bleaching Treatment of Discolored Dentition", Compend. Cont. Educ. Dent., 5 at 803-808 (1984).

Baumgarttner J. C., Reid D. E., Pickett, A. B., "Baumgartner Pulpal Reaction to the Modified McInnes Bleaching Technique", J. Endodon., 9 at 527-529 (1983).

Walton R. E., et al., "External Bleaching of Tetracycline-Stained Teeth in Dogs", J. Endodon., 8(12) at 536-542 (1982).

McEvoy S. A., "Chemical Agents for Removing Intrinsic Stains from Vital Teeth, II", Quintess. Int., 20(6) at 379-383 (1989).

Bailey R. W., Christen A. G., "Effects of a Bleaching Technic on the Labial Enamel of Human Teeth Stained with Endemic Dental Fluorosis", J. Dent. Res., 49 at 168 (1970).

Bailey R. W., Christen A. G., "Bleaching of Vital Teeth Stained with Endemic Dental Fluorosis", Oral Surg., Oral Med., Oral Pathol., 26(6) at 871-878 (1968).

Seals N. S., Wilson C. F. G., "Pulpal Response to Bleaching of Teeth in Dogs", Pediatr. Den, 7(3) at 209-214 (1985).

Croll T. P., Cavanaugh R. R., "Enamel Color Modifications by Controlled Hydrochloric Acid Pumice Abrasion; II. Further Examples", Quintess Int., 17(3) at 157-164 (1984).

Nathanson D., Parra, C., "Bleaching Vital Teeth: A Review and Clinical Study", Compend. Contin. Educ. Dent., 8(7) at 490-498 (1987).

Zach L., Cohen G., "Pulp Response to Externally Applied Heat", Oral Surg., Oral Med., Oral Pathol., 19(4) at 515-530 (1965).

Nyborg H., Brannstorm M., "Pulp Reaction to Heat", J. Prosthodon. Dent., 19(6) at 605-612 (1968).
Swerdlow H., Stanley H. R., "Reaction of the Human Pulp to Cavity Preparation Part II at 150,000 RPM with an Air-Water Spray", J. Pros. Dent., 1(9) at 121-131 (1959).
Cohen S. C., "Human Pulpal Response to Bleaching Procedures on Vital Teeth", Southern Journal of Endodontics, 5(5) at 134-138 (1979).
Robertson W. D., Melfi R. D., "Pulpal Response to Vital Bleaching Procedure", J. Endodon., 6(7) at 645-649 (1980).
Ledoux W. R., Malloy R. B., et al., "Structural Effects of Bleaching on Tetracycline-Stained Vital Rat Teeth", J. Prosthondont. Dent., 54(1) at 55-61 (1985).
Bowles W. H., Ugwuneri Z., "Pulp Chamber Penetration by Hydrogen Peroxide Following Vital Bleaching Procedure", J. Endodon., 13(8) at 375-377 (1987).
Stindt D. J., Quenette L., "An Overview of Gly-oxide Liquid: Control and Prevention of Dental Disease", Compend. Contin. Educ. Dent., 10(9) at 514-519 (1989).
Christensen G. J., "Subject: Tooth Bleaching, Home Use Products", Clinical Research Associates Newsletter, 7(13) at 1-4 (1989).
Griffin R. E., Grower M. F., Ayer W. A., "Effects of Solutions Used to Treat Dental Fluorosis on Permeability of Teeth", J. Endodon., 4(3) at 139-143 (1977).
Morrison S. W., "Vital Tooth Bleaching—The Patient's Viewpoint", Gen. Dent. at pp. 238-240 (May-Jun. 1986).
Christensen G., Christensen R., "Tooth Bleaching, Home Use Products", CRA Newsletter, 13(12) at 1-3 (1989).
Darnell D. J., Moore W. C., "Vital Tooth Bleaching—The White & Brite TM Technique", Compend. Contin. Educ. Dent., 11(2) at 86-94 (1990).
Link E. M., "The Mechanism of pH-Dependent Hydrogen Peroxide Cyctotoxicity in Vitro", Arch. Biochem., Biophys., 265(2) at 362-372 (1988).
Feiglin B., "A 6-Year Recall Study of Chemically Bleached Teeth", Oral Surg., Oral Med., Oral Pathol., 63(5) at 610-613 (1987).
Schraufstatter I., Hyslop P. A., Jackson J. H., et al., "Oxidant-Induced DNA Damage of Target Cells", J. Clin. Invest., 83(3) at 1040-1050 (1988).
Ayars G. H., Altman L. C., McManus M. M., et al., "Injurious Effect of the Eosinophil Peroxide-Hydrogen Peroxide-Halide System and Major Basic Protein on Human Nasal Epithelium in Vitro", Am. Rev. Respir. Dis., 140(1) at 25-131 (1989).
Tripathi B. J., Tripathi, R. C., "Hydrogen Peroxide Damage to Human Corneal Epithelial Cells In Vitro; Implications for Contact Lens Disinfection Systems", Arch. Opthalmol., 107(10) at 1516-1519 (1989).
Barchowsky A., Kent R. S., Whorton A. R., "Recovery of Porcine Aortic Endothelial Cell Prostaglandin Synthesis Following Inhibition by Sublethal Concentrations of Hydrogen Peroxide", Biochem. Biophys. Acta., 927(3) at 372-381 (1987).
Jordan R. E., Boksman L., "Conservative Vital Bleaching Treatment of Discolored Dentition", Compend. Contin. Educ. Dent., 10(5) at 803-805 (1984).
McKenna S. M., Davies K. J., "The Inhibition of Bacterial Growth by Hypochlorous Acid; Possible Role in the Bactericidal Activity of Phagocytes", Biochem. J., 254(3) at 685-692 (1988).
Nathan C. F., "Neutrophil Activation of Biological Surfaces; Massive Secretion of Hydrogen Peroxide in Response to Products of Macrophages and Lymphocytes", J. Clin. Invest., 80(6) at 1550-1560 (1987).
Klebanoff S. J., Agosti J. M., Jorg A., et al., "Comparative Toxicity of the Horse Eosinophil Peroxidase-$H_2O_2$-Halide System and Granule Basic Proteins", J. Immunol., 143(1) at 239-244 (1989).
MacCarthy K. G., Dahl V. M., "Inhibition of Growth of Trichophyton Rubrum by the Myeloperoxidase-Hydrogen Peroxide-Chloride Systems:, J. Invet. Dermatol., 92(4) at 639-641 (1989).
Paty P. B., Graeff R. W., Waldman F. M., et al., "Biologic Priming of Neutrophils in Subcutaneous Wounds", Arch. Serg., 123(12) at 1509-1513 (1988).
Garotta F., Talmadge K. W., Pink J. R., et al., "Functional Antagonism Between Type I and Type II Interferons on Human Macrophages", Biochem. Biophys. Res. Commun., 140(3) at 948-954 (1986).
Nathan C. F., "Respiratory Burst in Adherent Human Neutrophils: Triggering by Colony-Stimulating Factors CSF-GM and CSF-G", Blood, 73(1) at 301-306 (1989).
Kagaya K., Watanabe K., Fukazawa U., "Capacity of Recombinant Gamma Interferon to Activate Macrophages for Salmonella-Killing Activity", Infect. Immun. 57(2) at 609-615 (1989).

Bortolussi R., Vanderbroucke-Grauis D. M., "Relationship of Bacterial Growth Phase to Killing of Listeria Monocytogenes by Oxidative Agents Generated by Neutrophils and Enzyme Systems", Infect. Immun., 55(12) at 3197-3203 (1987).

Zoccarato F., Deana R., Cavallini L., et al., "Generation of Hydrogen Peroxide by Cerebral-Cortex Synaptosomes; Stimulation by Ionomycin and Plasma-Membrane Depolarization", Eur. J. Diochem., 180(2) at 473-478 (1989).

Sporn P. H. S., Peters-Golden M., Simon R. H., "Hydrogen-Peroxide-Induced Arachidonic Acid Metabolism in the Rat Alveolar Macrophage", Am. Rev. Respir. Dis., 137(1) at 49-56 (1988).

Denis D., Choo L. Y., Riendeau D., "Activation of 5-Lipoxygenase by Guanosine 5—O-(3-Thiotriphosphate and Other Nucleoside Phosphorothioates: Redox Properties of Thionucleotide Analogs", Arch. Bichem. Biophys., 273(2) at 592-596 (1989).

Hatzelmann A., Schatz M., Ullrich V., "Involvement of Glutathione Peroxidase Activity in the Stimulation of 5-lipoxygenase Activity by Gluthathione-depleting Agents in Human Polymorphonuclear Leukocytes", Eur. J. Biochem., 180(3) at 527-533 (1989).

Moore R. V., Brummit M. L., Mankad V. N., "Hydroperoxides Selectively Inhibit Human Erythrocyte Membrane Enzymes", Arch. Biochem. Biophys, 273(2) at 527-534 (1989).

Pruess-Schwartz D., Nimesheim A., Marnett L. J., "Peroxyl Radical-and Cytochrome P-450-dependent Metabolic Activation of (+)-7,8-Dihydroxy-7,8-dihydrobenzo(a)pyrene in Mouse Skin in Vitro and in Vivo", Cancer P.es., 49(7) at 1732-1737 (1989).

Marshansky V., "Organic Hydroperoxides at High Concentrations Cause Energization and Activation of ATP Synthesis in Motochondria", J. Biol. Chem., 264(7) at 3670-3673 (1989).

Meagher R. C., Salvado A. J., Wright D. G., "An Analysis of the Multilineage Productin of Human Hematopoietic Progenitors in Longterm Oxygen Intermediates Derived from Mature Phagocytic Cells Have a Role in Limiting Progenitor Cell Self-Renewal", Blood, 72(1) at 273-281 (1988).

Metodiewa K., Reszka K., Donford H. B., "Evidence for a Peroxidatic Oxidation of Norepinephrine, a Catecholamine, by Lactoperoxidase", Biochem. Biophys. Res. Commun., 160(3) at 1183 (1989).

White C. S., Jackson J. H., McMurtry, I. F., et al., "Hypoxia Increases Glutathione Redox Cycle and Protects Rat Lungs Against Oxidants", J. Appl. Physil., 65(6) at 2607-2616 (1988).

Messana J. M., Cieslinski D. A., O'Connor R. P., et al., "Glutathione Protects Against Exogenous Oxidant Injury to Rabbit Renal Proximal Tubules", Am. J. Physiol., 255(5) at F874-F884 (1988).

Buckley B. J., Tanswell A. K., Freeman B. A., "Liposome-Mediated Augmentation of Catalase in Alveolar Type II Cells Protects Against $H_2O_2$ Injury", J. Appl. Physiol., 3(1) at 359-367 (1987).

Galaris D., Cadenas E. and Hochstein P., Redox Cycling of Myoglobin and Ascorbate: A Potential Protective Mechanism Against Oxidative Reperfusion Injury in Muscle", Arch. Biochem. Biophys. 273(2) at 497-504 (1989).

Scott M. D., Eaton J. W., Kuypers F. A., et al., "Enhancement of Erythrocyte Superoxide Dismutase Activity: Effects on Cellular Oxidant Defense", Blood, 74(7) at 2542-2549 (1989).

Gillespie M. N., Moore C. G., Wright, C. E., et al., "Salutary Effects of Prostaglandin $E_1$ in Perfused Rat Lungs Injured with Hydrogen Peroxide", J. Pharmacol. Exp. Ther., 24(1) at 1-5 (1987).

Gaetani G. F., Galiano S., Canepa L., et al., "Catalase and Glutathione Peroxidase are Equally Active in Detoxification of Hydrogen Peroxide in Human Erythrocytes", Blood, 73(1) at 334-339 (1989).

DeLange R. J. and Glazer A. N., "Phycoerythrin Fluorescence-Based Assay for Peroxy Radicals: A Screen for Biologically Relevant Protective Agents", Anal. Biochem., 177(2) at 300-306 (1989).

Maddipati K. R., Gasparski C., Marnett L. J., "Characterization of the Hydroperoxide-Reducing Activity of Human Plasma", Arch. Biochem. Biophys., 254(1) at 9-17 (1987).

Yasuda H., Miki M., Takenaka Y., et al., "Changes in Membrane Constituents and Chemiluminescence in Vitamin E-Deficient Red Blood Cells Induced by the Xanthine Oxidase Reaction", Arch. Biochem. Biophysc., 272(1) at 81-87 (1988).

Richards D. M. C., Dean R. T., Jessup W., "Membrane Proteins are Critical Targets in Free Radical Mediated Cytolsis", Biochem. Biophys., Acta., 946(2) at 281-288 (1988).

Nakaya H., Tohse N., Kanno M., "Electrophysiological Derangements Induced by Lipid Peroxidation in Cardiac Tissue", Am. J. Physiol., 253(5pt2) at H1089-1097 (1987).

Tayarani I., Chaudiere J., Lefauconnier J-M., "Enzymatic Protection Against Peroxidative Damage in Isolated Brain Capillaries", J. Neurochem., 48(5) at 1399-1402 (1987).

Minotti, G., "tert-Butyl Hydroperoxide-Dependent Microsomal Release of Iron and Lipid Peroxidation: II. Evidence for the Involvement of Nonheme, Nonferritin Iron in Lipid Peroxidation", Arch. Biochem. Biophys., 273(1) at 144-147 (1989).

Fraga C. F., Zamora R., Tappel A. L., "Damage to Protein Synthesis Concurrent with Lipid Peroxidation in Rat Liver Slices: Effect of Halogenated Compounds, Peroxides and Vitamin E", Arc. Biochem. Biophys., 270(1) at 84-91 (1989).

Masaki N., Kyle M. E., Farber J. L., "tert-Butyl Hydroperoxide Kills Cultured Hepatocytes by Peroxidizing Membrane Lipids", Arch. Biochem. Biophys., 269(2) at 390-399 (1989).

Fraga C. F. and Tappel A. L., "Damage to DNA Concurrent with Lipid Peroxidation in Rat Liver Slices", Biochem. J., 252(3) at 893-896 (1988).

Junod A. F., "Effects of Oyxgen Intermediates on Cellular Functions", Am. Rev. Respir. Dis., 135(6 Pt 2) at S32-S34 (1987).

Amigoni N. A., Johnson G. K., Kalkwarf K. L., "The Use of Sodium Bicarbonate and Hydrogen Peroxide in Periodontal Therapy: A Review", J. Am. Dent. Assoc., 114(2) at 217-222 (1987).

Wennstrom J. L., Dahlen G., Grondahl K., et al., "Periodic Subgingival Antimicrobial Irrigation of Periodontal Pockets: II. Microbiological and Radiographical Observations", J. Clin. Periodontal, 14(10) at 573-580 (1987).

Wennstrom J. L., Heijl L., Dahlen G., et al., "Periodic Subgingival Antimicrobial Irrigation of Periodontal Pockets: I. Clinical Observations", J. Clin. Periodontal, 14(9) at 541-550 (1987).

Gusberti F. A., Sampathkumar P., Siegrist B. E., et al., "Microbiological and Clinical Effects of Chlorhexidine Digluconate and Hydrogen Peroxide Mouthrinses on Developing Plaque and Gingivitis", J. Clin. Periodontal, 15(1) at 60-67 (1988).

Boyd R. L., "Effects on Gingivitis of Daily Rinsing with 1.5% $H_2O_2$", J. Clin. Periodontal, 16(9) at 557-562 (1989).

Whitehead S. P., Watts T. L. P., "Short-term Effect of Keyes' Approach to Periodontal Therapy Compared with Modified Widman Flap Surgery", J. Clin. Periodontal, 14(10) at 599-604 (1987).

Herrin J. R., Squier C. A., Rubright W. C., "Development of Erosive Gingival Lesions after Use of a Home Care Technique", J. Periodontal, 55(11) at 785-788 (1987).

Ramp W. K., Arnold R. R., Russell J. E., et al., "Hydrogen Peroxide Inhibits Glucose Metabolism and Collagen Synthesis in Bone", J. Periodontal, 58(5) at 340-344 (1987).

Weitzman, S. A., Weitberg A. B., Stossel T. P., et al., "Effects of Hydrogen Peroxide on Oral Carcinogenesis in Hamsters", J. Periodontal, 5711 at 685-688 (1986).

Rees T. D. and Orth C. F., "Oral Ulcerations with Use of Hydrogen Peroxide", J. Periodontal, 57(11) at 689-692 (1986).

Jan Rundegren, Jan Fornell and Thorild Ericson, "In vinvo and in vitro studies on a new perioxide-containing toothpaste", Scand. J. Dent. Res. 81, 543-7 (1973).

C. B. Atkinson, "Hints, Queries and Comments: Pyrozone", The Dental Cosmos, pp. 330-332 (1893).

Richard R. Seals, et al., "Custom Mount Protectors: A Review of Their Applications", J. Prosthetic Dent. 51(2) at 238-242 (1984).

Gye Ju Rhee, et al., "Carbamide Peroxide", Yak Hak Hoeji 28(6), 299-303 (1984).

METHOD AND MATERIAL FOR BRIGHTENING TEETH

Matter enclosed in heavy brackets [ ] appears in the original patent but forms no part of this reissue specification; matter printed in italics indicates the additions made by reissue.

This application is a continuation of application Ser. No. 235,304, filed Aug. 23, 1988, now abandoned.

FIELD OF THE INVENTION

This invention relates to a brightening agent and process for brightening teeth, and more particularly to such a process that is user activated and controlled.

DESCRIPTION OF PRIOR ART

There is no need to dwell on the cosmetic desires of people to have bright teeth. Over the years many processes have come and gone, each promising a new breakthrough in teeth brightening. In general, the processes that work are too costly to use, or require special training or are harsh on the teeth.

Since tooth stains stem from a large variety of causes, from poor oral hygiene to the use of drugs (such as tetracycline), to the smoking of tobacco products, a universal solution has evaded dentistry. One process for brightening the stains caused by tetracycline is shown in the Copendium of Continuing Education (Endodontal) Vol. V, No. 6, June 1984, page 465. This multi-page brochure outlines the steps a trained professional should take to perform the process of brightening stained teeth. The results of this process are mixed at best. The Compendium which is hereby incorporated by reference, contains a discussion of teeth bleaching techniques, all of which require the application of heat.

The tooth brightening processes available today rely upon some physical manipulation of the teeth. The process described in the above-mentioned publication is one example. Another example is the use of bonding to cover stained teeth. A common step in all such processes is that a trained professional must perform every step of the process. It is the professional who controls the ultimate color of the teeth and not the patient.

Thus, it is clear that a need exists in the art for a product and process that can be used safely by any person and whereby the user can control the degree of brightness of the teeth.

A further need exists in the art for a process of tooth brightening, coupled with a system for protecting the brightened teeth from reverting back to their original dull or stained appearance, the entire system being under control of the user.

The foregoing has outlined some of the more pertinent objects of the present invention. These objects should be construed to be merely illustrated of some of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

I have discovered that [peroxide compounds] *certain compositions, namely those capable of sustained nascent oxygen release,* which have been commercially available for a number of years and used by professionals and others for a wide variety of purposes have an unexpected result when used in a very specific manner.

While it is true that hydrogen peroxide has been known for years to act as a cleanser for teeth, it is also true that the rapid decomposition of hydrogen peroxide has limited its usefulness. Indeed, the procedure discussed above for cleansing tetracycline stains takes into account this well-known deficiency of hydrogen peroxide.

The commercial product PROXIGEL®, described in U.S. Pat. No. 3,657,413 issued on Apr. 18, 1972 to M. W. Rosenthal, which patent is hereby incorporated herein by reference, is one attempt to overcome the problems of hydrogen peroxide by using urea peroxide in a slowly dispersable glycerol based solvent. This combination, according to the above-mentioned patent, improves sustained nascent oxygen release. It is the nascent oxygen release which is believed to cause the antiseptic and/or cleansing effect of the peroxide. PROXIGEL®, which is manufactured by Reed & Carnrick, is a 10% solution of carbamide peroxide in a water free gel base.

The problem with peroxides is well stated in the Rosenthal patent as follows:

The principal limitation of commonly used peroxide aqueous solutions, however, is their brief period of contact and function [an] *on* oral tissues. Since many oral bacteria, as well as saliva, contain high concentrations of the enzyme catalase and other peroxides, the hydrogen peroxide is rapidly decomposed into gaseous oxygen and water. It is a well known fact that the antibacterial effects of peroxide are exercised only at the instant that the peroxide decomposes to release nascent oxygen. The gaseous oxygen molecules subsequently formed by combination of the nascent oxygen atoms have no antibacterial effects or tissue oxygenating potential. Thus, there is only transitory contact of the active oxygenating agent with the affected tissues. Furthermore, the low viscosities of water solutions of hydrogen peroxide itself and the water solutions of hydrogen peroxide-active salts, do not allow the active material to stay in contact with affected tissues for as long as is desirable because of the constant flushing effects of salivary secretions. This tendency toward rapid decomposition of $H_2O_2$ into gaseous oxygen and water and the rapid removal of peroxide solutions has severely limited their application to, and utility on, oral tissues.

It would be highly desirable, therefore, to extend the period of oxygen release from hydrogen peroxide for considerably longer periods, as well as to increase the period of retention on tissues.

The Rosenthal patent then goes on to describe a gel form of the peroxide to allow longer action of the peroxide. The purpose of the Rosenthal product is for tissue cleansing and antiseptic use. Subsequent patents, such as U.S. Pat. No. 4,431,631 and [4,537,413] *4,537,778*, issued Feb. 14, 1984 and Aug. 27, [1986] *1985*, respectively, deal with the same problem and solve it by creating various aerating gels for longer adherence to the tissue, *among them being PEROXYL® gel.*

In contrast to the prior art, the process of this invention begins with a professional making a splint for the user. The splint is, advantageously, made from a clear, very thin plastic material and is designed to extend onto the user's gingiva and to fit tightly thereto so as to minimize [air or] saliva from impacting the enclosed teeth. The splint is designed to fit one or more teeth as desired. The user then places a drop or two of the cleanser solution such as the peroxide based PROXIGEL® solution discussed above) into the splint and places the splint, with the solution inside, around the tooth or teeth and over a portion of the gingiva.

The patient then wears the splint for a number of hours, removes the splint, rinses the teeth, preferably with a fluoride [compound] *composition*, and then, repeats the process, *reintroducing the splint with the new brightener agent in substantially liquid tight engagement into the mouth*. Those users who wish to brighten their teeth slowly will wear the splint only while sleeping. This method will usually take about four weeks to show dramatic results. Others, who desire faster whitening, may choose to wear the splint during the day as well. This is possible because of the transparent, thin nature of the splint. [When] *After a number of days when* the degree of brightness desired by the user is achieved, the user stops using the splint.

The tightly fitting splint serves the dual purpose of physically restraining the solution from evaporating or migrating away from the teeth, and also preventing the destruction of the oxygenating properties of the peroxide. Dramatic results have been demonstrated with this procedure.

Thus, it is a feature of my invention to have a professional prepare for the user a splint designed to tightly fit around the tooth or teeth to be brightened *in substantial liquid-tight engagement*, have the user place a solution of peroxide within the tooth cavity formed in the splint and then to insert the splint around the proper tooth or teeth. *By the term "substantially liquid tight", I mean engagement between a custom-made splint and the teeth-/tooth effectively tight to (a) minimize saliva from impacting the teeth/tooth enclosed within the splint, (b) restrain physically the cleaning/brightening solution from evaporating or migrating away from the teeth, and (c) prevent the destruction of the oxygenation properties of the peroxide.* The user then periodically replenishes the peroxide and repeats the process until the desired amount of brightness is achieved.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be [head] *made* to the following detailed description taken in connection with the accompanying drawings in which.

Similar reference characters refer to similar parts throughout the several views of the drawings.

DETAILED DISCUSSION

Figure 1:
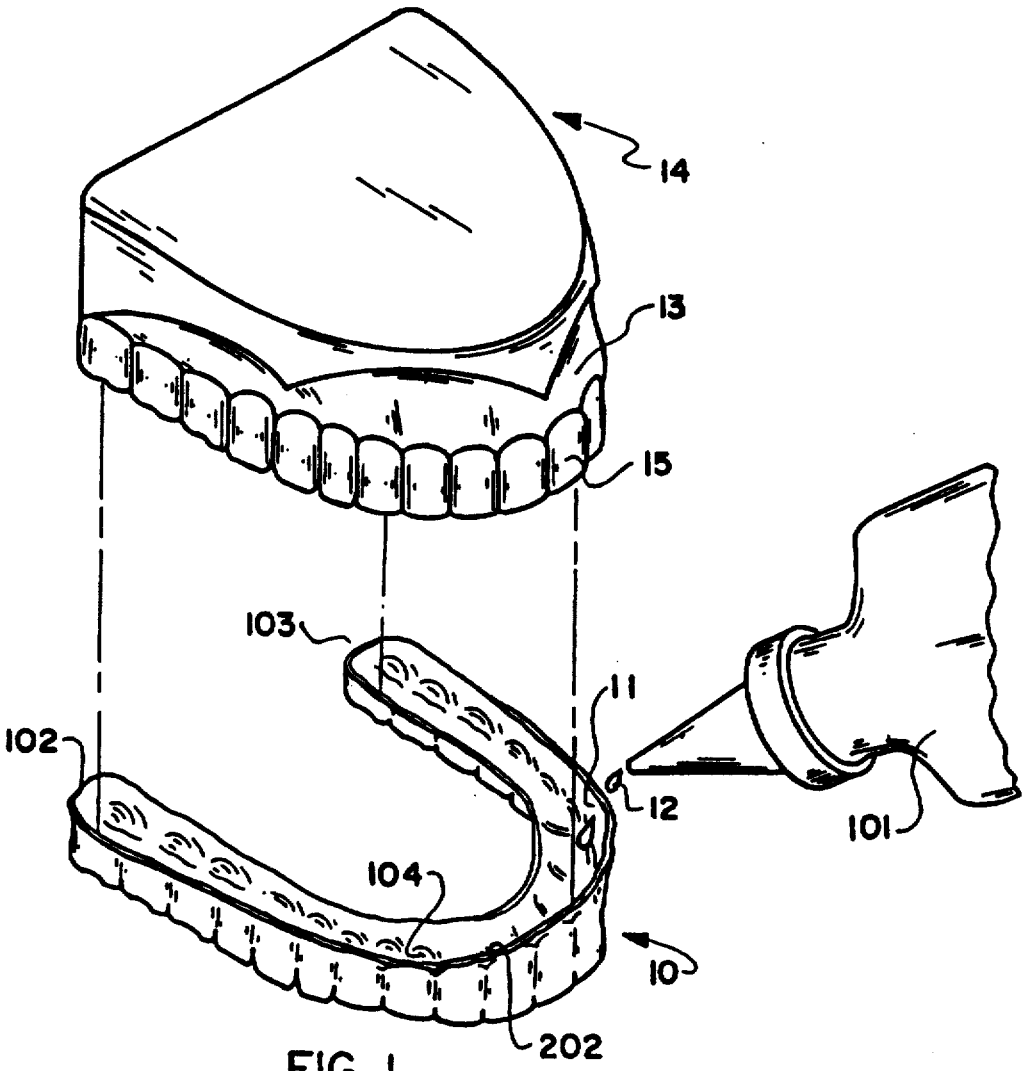
FIG. 1 shows a set of upper teeth and a full splint therefore.

FIG. 1 illustrates a mold 14 a full tooth mold made in a traditional way by the dentist. In this discussion, we can assume that mold 14 is in fact a representation of the actual mouth of a patient having gingiva 13 with teeth 15 extending therefrom. Of course, in our example mold 14 contains all of its teeth. This, as will be seen, is not necessarily critical to the functioning of the invention. In addition, many people have teeth which are not fully aligned. This again, is not a problem, since the splint, (as will be discussed) will allow for individual tooth differences. FIG. 1 also shows splint 10 made by the dental professional in a manner to be more fully detailed hereinafter. At this point, it is sufficient to note that splint 10 has sealed end portions 102 and 103 and inter proximal portions 104 within the splint 10. The person wishing to brighten his or her teeth obtains the cleaning solution 101 (which will be discussed in more detail hereinafter) and places within the tooth cavity 11 of the splint a few drops 12 of the solution.

Figure 2:
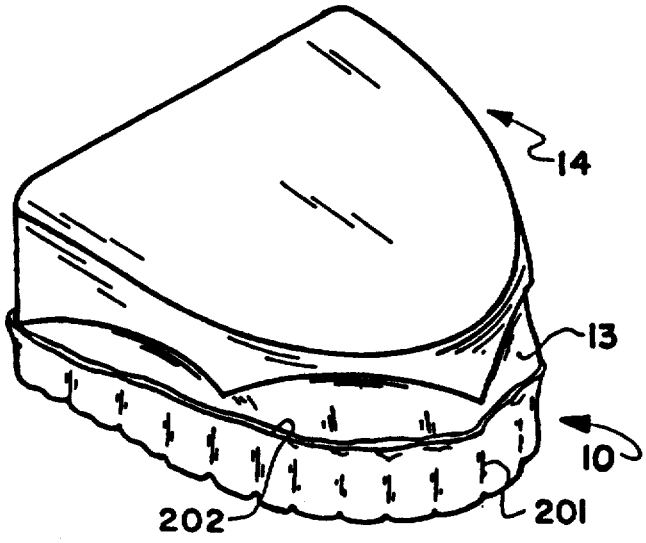
FIG. 2 shows the splint positioned on the teeth.

As shown in FIG. 2, the splint is then positioned by the user around teeth 15 and gingiva 13 making a substantially [air-tight] *liquid-tight* seal 202 between the top portion of splint 10 and gingiva 13.

Figure 3:
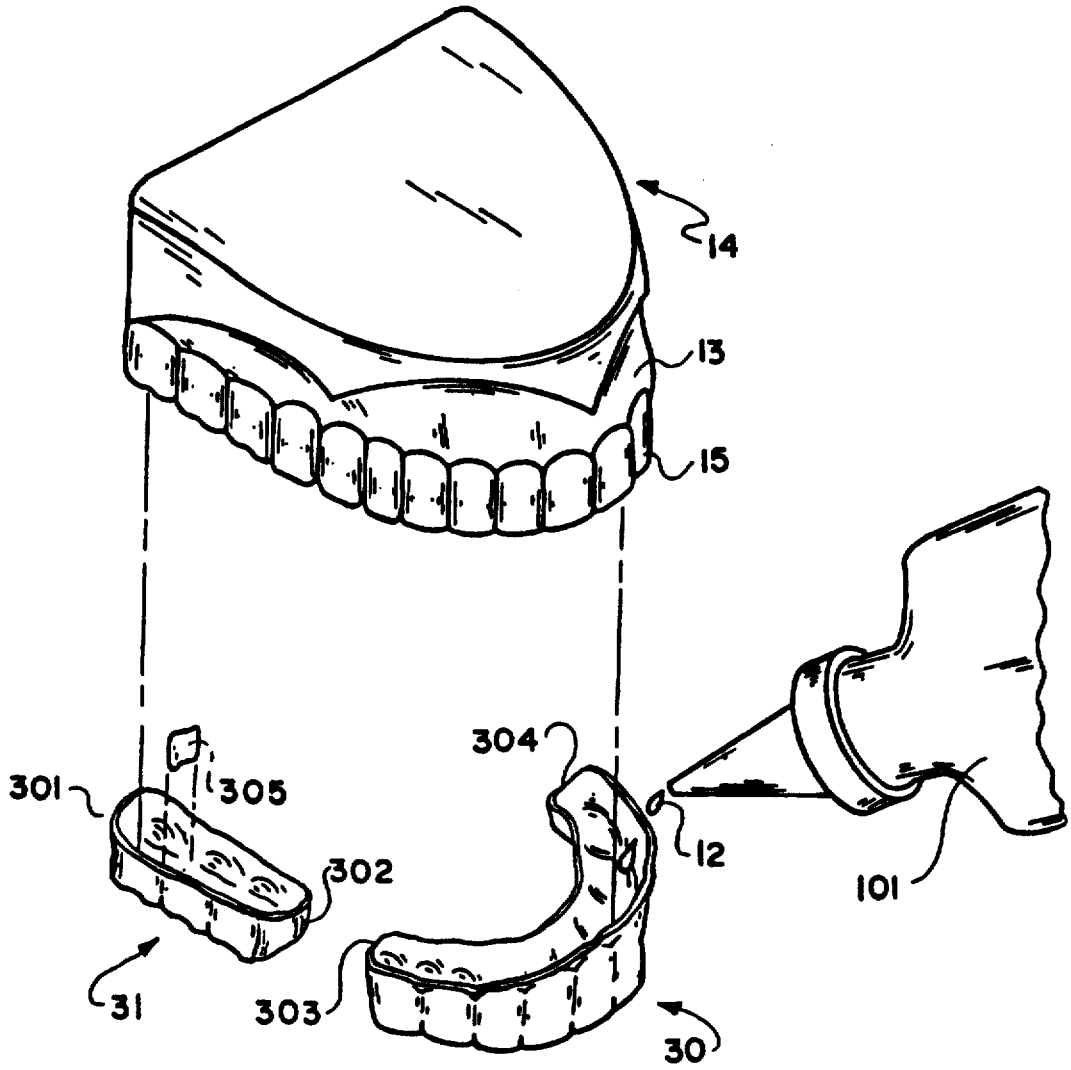
FIG. 3 shows a set of upper teeth and two partial splints therefore; and the two partial splints of FIG. 3 positioned on the teeth.

FIG. 3 shows the same mouth mold 14 with two partial splints 30 and 31. Splint 30 covers some of the front teeth whole splint 31 covers three of the molars. It should be noted the splints 30 and 31 can be constructed to cover any number of teeth, from a single tooth to a full splint. The ends of splint 30 have closed end portions 303 and 304 formed to prevent cleansing solution 12 from leaking out of the splint. Splint 31 has end portions 301 and 302 similarly designed.

Figure 4:
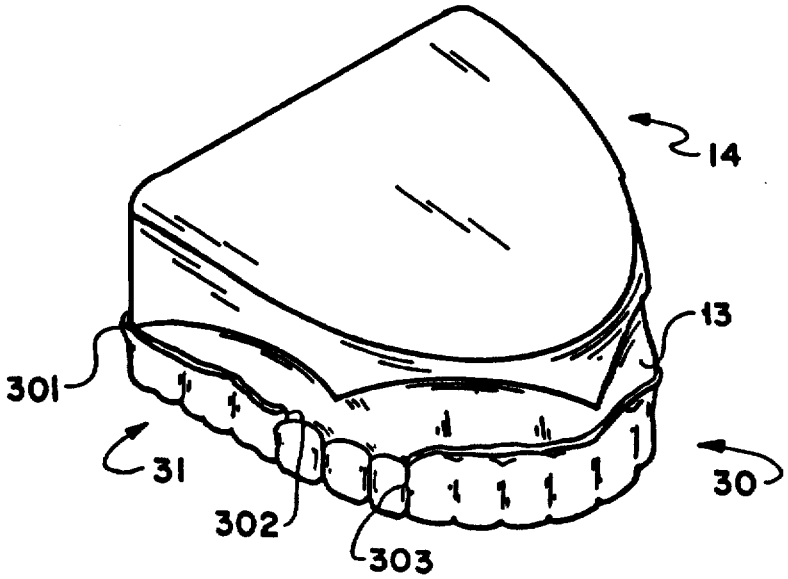

*The mold 14 in* FIG. 4 shows partial splints 30 and 31 positioned around their respective teeth *with gingiva area 13*, each forming a substantially [air] *liquid* tight seal with their adjacent gingiva. *Again as in FIG. 3 partial splints 30 and 31 have closed end portions 302 and 303.*

Once the splint is in place, the user then wears the splint for a number of hours, removes the splint, rinses the teeth, preferably with a fluoride [compound] *composition*, and then repeats the process. For users who wish to brighten their teeth slowly, wearing the splint only while sleeping will suffice. This method will usually take about four weeks to show dramatic results. Others, who desire faster whitening, may choose to wear the splint during the day as well. This is possible because of the transparent, thin nature of the splint. When the degree of brightness desired by the user is achieved, the user stops wearing the splint.

One method of creating the splint includes the following steps:

(a) making a mold of the tooth or teeth to be cleaned in the traditional manner, well-known to dental professionals and as shown in FIG. 1;

(b) obtaining a sheet of plastic material of the appropriate size and between 0.01 inch and 0.1 inch thick depending upon the application;

(c) placing the sheet in a holder;

(d) spraying silicone on both sides of the plastic sheet;

(e) heating the plastic sheet on one side only until it becomes clear;

(f) placing the clear plastic over the prepared model (missing teeth can be replaced with denture teeth or metal crown forms) or over only the teeth representative of the teeth to be cleaned.

(g) immediately pressing molding putty against the heated plastic, using fingers to contour the heated plastic over the model;

(h) removing the model and trimming the plastic; and (i) sealing the ends of the splint to minimize [air and] saliva from entering and to minimize solution from leaking (or [bring] *being* sucked) out.

Another method of forming the splint would be to use the omnivac method now commonly employed in dentist offices for other dental applications. It is important to note, however, that any method of constructing a splint is acceptable. Advantageously, the splint should be resilient to allow the user to remove and replace the splint around the tooth or teeth.

The solution that is inserted in the splint can be selected from the peroxy compounds, and can be the above-mentioned PROXIGEL® oral cleanser. One drop per tooth has shown to be sufficient to begin the cleaning process. Renewing the solution every 4 hours has shown to be effective in substantially brightening teeth within two weeks to a point where the difference in brightness (before and after) is readily apparent even to the untrained eye. The longevity of the brightness, or to say if the other way, the amount of time it takes for the stains or yellowing to return will depending upon conditions in the mouth.

This procedure has been demonstrated to clean yellow teeth, teeth dark from tetracycline, dark from reaction to orthodontics and teeth dark from unknown causes. In most situations, the compound used was a 10% solution of carbamide peroxide. Tests have shown the preferred cleaning solution to be [peroxyl] *PEROXYL*® gel mixed with [peroxigel] *PEROXIGEL*® in a ratio of 3 [millileters] *milliliters* of [peroxyl] *PEROXYL*®gel to 1.2 ounces of [peroxyl] *PROXIGEL*®. Greater than 3 milliliters of [peroxyl] *PROXIGEL*® reduces the viscosity to a point where it is not easily retained in the splint. Stannous fluoride *compositions*, or other fluoride(s) *compositions* can be mixed with the cleaner to provide greater benefits, if desired. Other compounds used with this method have shown good results.

One advantage of this procedure is that the teeth are cleaned uniformly and at the same time. Thus, a person does not have each tooth a different color, even for a few days. This is of particular importance where teeth are misaligned or not straight. The splint [holes] *holds* the cleaning solution against the teeth and even brightening is achieved. Of course, when and if it is observed that one portion of teeth is becoming brighter than another, the splint can be modified to allow different amounts of fluid into contact with different teeth. This can be done with separate splints, or with splints divided into sections internally by physical barriers. The physical barriers can be part of the splint structure or added temporarily for periods of time. This is shown by barrier 305 in FIG. 3. Barrier 305 can be, for example, [cemented] *placed* in position between teeth to allow for separate application of cleansing material in each section. The dental professional can adjust the positioning of the barrier by removing and [recementing] *replacing* the barrier, or by other means.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. The process of brightening teeth *during sleep at night,* comprising the steps of:

obtaining a substantially liquid tight splint to cover the tooth or teeth to be brightened;

placing within said splint a brightener agent at the location within said splint associated with the tooth [surfaces] *or teeth* to be brightened; and

*before sleep,* placing the splint containing said brightener agent around the tooth or teeth to be brightened *for a sufficient number of nights to effect a substantial brightening of said tooth or teeth.*

2. The process of claim 1 wherein *the* brightener agent is a nonaqueous [oral] peroxy [compound] *composition.*

3. The process of claim 2 wherein said brightener agent is mixed with stannous fluoride.

4. The process of claim 2 wherein said [oral] peroxy [compound] *composition* is [peroxyl] *PEROXYL*® gel mixed with [peroxigel] *PROXIGEL*® in the ratio of about 3 milliliters of [peroxyl] *PEROXYL*® *gel* to about 1.2 ounces of [proxigel] *PROXIGEL*®.

5. The process of claim [1] *19* further comprising the steps of:

periodically removing said splint;

adding additional brightener agent; and replacing said splint containing said additional brightener agent around the tooth or teeth to be brightened.

6. The invention set forth in claim [5 wherein said periodically removing step includes the step of obtaining a fresh unused substantially airtight splint to cover the tooth or teeth to be brightened, and wherein said replacing step, includes the step of substituting said fresh splint for said removed splint] *1, further comprising the steps of:*

*periodically removing said splint from said tooth or teeth;*

*replacing the used brightener agent with new brightener agent and;*

*reintroducing the splint with the new brightener agent with said tooth or teeth.*

7. The invention set forth in claim 1 where the splint obtaining step includes the steps of:

making an impression of the tooth or teeth to be brightened, said impression including adjacent gingiva;

molding said impression to create a mold of said tooth or teeth to be brightened;

forming plastic tightly around said mold; and trimming said formed plastic to fit over said tooth or teeth to be brightened and over said adjacent gingiva.

8. The invention set forth in claim 7 wherein said trimmed plastic is between 0.01 inch and 0.1 inch thick.

9. The invention set forth in claim 7 wherein said trimmed plastic is transparent.

10. The use of a [peroxy compound] *composition capable of sustained nascent oxygen release* to bleach teeth, wherein the use [consists of] *comprises:* bringing said [peroxy compound] *composition* into physical contact with each said tooth [to be cleaned] *for sufficient amount of time to effect substantial brightening;*

[creating] *whereby said composition is retained by* a mechanical barrier around said [peroxy compound after] *composition during* said physical contact [is made], said mechanical barrier relying upon intimate contact with the gingiva adjacent the tooth for a substantially [airtight and] leakproof seal.

11. The use of a peroxy [compound] *composition* as set forth in claim 10 wherein physical contact is made with a plurality of teeth at the same time and wherein said mechanical barrier extends to all of said plurality of teeth.

12. The use of a peroxy [compound] *composition* as set forth in claim 11 wherein said mechanical barrier contour provides means for allowing continued physical contact of different amounts of said peroxy [compound] *composition* for different teeth.

13. The use of a peroxy [compound] *composition* as set forth in claim 12 wherein said last mentioned means is adjustable.

14. The use of a peroxy [compound] *composition* as set forth in claim 10 wherein said mechanical barrier is a splint obtained by the steps of:

making an impression of the tooth or teeth to be brightened, said impression including adjacent gingiva;

molding said impression to create a mold of said tooth or teeth to be brightened;

forming plastic tightly around said mold; and trimming said formed plastic to fit over said tooth or teeth to be brightened and over said adjacent gingiva.

15. The use of a peroxy [compound] *composition* as set forth in claim 14 wherein said trimmed plastic is transparent.

16. The use of a [peroxy compound] *composition* as set forth in claim 10 wherein said compound is a mixture of [peroxyl] *PEROXYL® gel* and [peroxigel] *PROXIGEL®* in the ratio of *about* 3 milliliters of [peroxyl] *PEROXYL® gel* to *about* 1.2 ounces of [peroxigel] *PROXIGEL®*.

*17. The process of claim 2 wherein said nonaqueous peroxy composition contains carbamide peroxide and is in a water-free gel base.*

*18. The process of claim 1 in which the splint is placed around the tooth or teeth to be brightened during sleeping for about four weeks.*

*19. The process of claim 1 in which, in addition to placing said splint containing said brightening agent before sleep at night, said splint is also placed around the tooth or teeth during the day as well.*

*20. The process of claim 19 in which during the day the brightening agent is renewed several times, each renewal after several hours.*

*21. The process of claim 20 in which during the day the brightening agent is renewed during the day about every four hours.*

*22. The process of claim 20 or 21 in which said splint is used during the daytime and during sleeping for at least about two weeks.*

*23. The process of substantially brightening teeth during sleep at night and during the day, comprising the steps of:*

*(a) obtaining a substantially liquid tight splint to cover the tooth or teeth to be brightened;*

*(b) placing within said splint a brightener agent at the location within said splint associated with and for physical contact with each tooth or teeth to be substantially brightened, said brightener agent comprising a non-aqueous peroxy composition;*

*(c) before sleep, and during the day as well, placing the splint containing said peroxy brightener agent around the tooth or teeth to be substantially brightened, so as to create a mechanical barrier around the peroxy composition brightener after said physical contact is made, said mechanical barrier relying upon intimate contact with the gingiva adjacent the tooth or teeth for a substantially liquid tight seal, said placement occurring for a sufficient number of nights and days to effect a substantial brightening of said tooth or teeth.*

*24. The process of claim 23 wherein the non-aqueous peroxy composition further contains carbamide peroxide and is in a water-free gel base.*

*25. The process of claim 23 in which the brightener agent is renewed several times during the day, each renewal after several hours.*

*26. The process of claim 23 in which the brightener agent is renewed several times during the day, each renewal after about four hours.*

*27. The process of claim 25 or 26 in which said splint is used during the daytime and during the nighttime for at least about two weeks.*

*28. The method of use of claim 10, wherein the composition capable of sustained release contains carbamide peroxide.*

*29. The method of use of claim 10, wherein the composition comprises a mixture of PEROXYL® gel and PROXIGEL®, where the volume ratio of PEROXYL GEL® to PROXIGEL® is about 3 milliliters to about 1.2 ounces.*

*30. The use of a composition capable of sustained nascent oxygen release to brighten teeth, wherein the use comprises:*

*bringing said composition into physical contact with a sufficient portion of the surface of each tooth to be brightened for a sufficient amount of time to effect substantial brightening of said tooth; and*

*retaining said composition by a mechanical barrier around said composition, said mechanical barrier being substantially liquid tight.*

*31. The use of claim 30, wherein the composition contains carbamide peroxide.*

*32. The use of claim 31, wherein the composition comprised a mixture of PEROXYL® gel and PROXIGEL®, wherein the volume ratio of PEROXYL® gel to PROXIGEL® is about 3 milliliters to about 1.2 ounces.*

*33. The use of claim 30, wherein said composition contains carbamide peroxide, and the mechanical barrier relies upon intimate contact with the gingiva adjacent the tooth.*

*34. The use of claim 30, wherein said mechanical barrier comprises a very thin, clear, plastic splint.*

*35. Composition comprising a mixture of PEROXYL® gel and PROXIGEL®, where the volume ratio of*

*PEROXYL® gel to PROXIGEL® is about 3 milliliters to about 1.2 ounces.*

*36. The use of a thin plastic splint in a process to accomplish substantial brightening of a tooth or teeth, comprising:*

*(a) placing within a custom fitted and trimmed, thin plastic splint a brightener agent at a location within said splint associated with and for physical contact with each tooth or teeth to be substantially brightened, said thin plastic splint custom-formed and adapted to said tooth or teeth so as to be in substantially liquid tight engagement when in engagement with said tooth or teeth; and*

*(b) placing said splint in substantially liquid tight engagement with said brightener agent on said tooth or teeth to be brightened for a time sufficient to effect substantial brightening of said tooth or teeth.*

*37. The use set forth in claim 36 wherein said trimmed plastic is between 0.01 inch and 0.1 inch thick.*

*38. The invention set forth in claim 36 wherein said trimmed plastic is transparent.*

*39. In a tooth brightening article combination, the combination comprising:*

*(a) a thin wall splint usable for up to about four weeks by the user, said splint being formed of plastic to fit in liquid tight configuration to a predetermined tooth or teeth, the ends of the splint being closed to prevent any substantial leakage of a liquid; and*

*(b) a liquid composition capable of sustained nascent oxygen release, said liquid composition being in sufficient quantity to be in physical contact with each predetermined tooth or teeth with said thin wall splint is fitted in said liquid tight configuration with said tooth or teeth.*

*40. The tooth brightening article combination of claim 39 wherein said splint has a wall thickness of 0.01 inch to 0.1 inch.*

*41. In a tooth brightening article combination, the combination comprising:*

*(a) a thin wall splint of plastic usable for up to about four weeks by the user, said splint being formed and trimmed on a mold of a selected tooth or teeth and surrounding gingiva, the trim of said splint being such that the thin wall plastic covers at least a part of the mold section representing gingiva surrounding said tooth or teeth to form a liquid tight seal therewith, and*

*(b) a gel base peroxy composition containing carbamide peroxide.*

*42. The tooth brightening article combination of claim 41, wherein said composition is a mixture of about 3 milliliters PEROXYL® gel to about 1.2 ounces of PROXIGEL®.*

*43. A splint for use in holding a liquid tooth brightening composition in a liquid tight seal against a selected tooth or teeth and surrounding gingiva, said splint comprising a sheet of plastic material of determined size and thickness of 0.01 inch to 0.1 inch and heat formed over a mold of said tooth or teeth and surrounding gingiva, to contour the plastic to said tooth or teeth and gingiva, the thus formed plastic trimmed to extend at least partially onto the surrounding gingiva and sealed at its end(s) to form a liquid tight seal when in place around said tooth or teeth, said splint usable daily for about four weeks by the user.*

*44. A thin formed plastic splint for minimizing saliva from entering and for minimizing a solution for brightening teeth from leaking out from a selected tooth or teeth when said splint is in place, said thin formed plastic splint being formed by:*

*(a) making a mold of the selected tooth or teeth and surrounding gingiva;*

*(b) placing a sheet of plastic material around said mold of said tooth or teeth section to be brightened and forming the plastic material to the contour of said tooth or teeth and surrounding gingiva section;*

*(c) trimming the plastic so that it extends at least partially onto the surrounding gingiva of said tooth or teeth; and*

*(d) sealing the ends of the splint to minimize a solution in the thus formed splint from leaking.*

*45. The thin formed splint of claim 44, including, prior to placing the sheet of plastic material around the mold of said tooth or teeth section, spraying silicone on both sides of the sheet and heating the plastic sheet.*

*46. The thin formed splint of claim 44 wherein the thickness of the plastic material is 0.01 to 0.1 inch.*

*47. A method of brightening teeth comprising:*

*(a) fitting the tooth or teeth to be brightened with a thin wall splint suitable for containing a source of releasable nascent oxygen, said splint comprising a plastic material having a wall thickness from between about 0.01 inch and about 0.1 inch and said splint further comprising a closed chamber around said tooth or teeth to be brightened, and having a top portion thereof in tight contact with the gingiva contiguous with the tooth or teeth to be brightened contained in said chamber, between said top portion of said splint forms an effective seal with said gingiva, such that release of nascent oxygen from a source therefore in said chamber is substantially restricted to said chamber and contact of said released nascent oxygen with the tooth or teeth in the chamber is (are) assured substantially free from the flushing effect of salivary secretions normally present in the mouth;*

*(b) placing within said splint a source of nascent oxygen;*

*(c) securing the splint containing said source of nascent oxygen to the tooth or teeth gingiva to be treated;*

*(d) maintaining said splint in the mouth until the source of nascent oxygen in the splint is substantially exhausted; and*

*(e) repeating steps (b) through (d) until the desired degree of brightness is obtained.*

*48. A tooth brightening, thin wall splint, suitable for use with a source of nascent oxygen said splint forming a closed chamber around tooth or teeth to be brightened, and said splint having (a) a wall thickness from between about 0.01 inch to about 0.1 inch, and (b) a top portion in tight contact with the gingiva contiguous to the tooth or teeth to be brightened, wherein said top portion of said splint forms an effective seal with said gingiva, such that release of nascent oxygen from a source located within said chamber is substantially restricted to said chamber and contact of said released nascent oxygen with the tooth or teeth in the chamber is (are) assured substantially free from the flushing effects of salivary secretions normally present in the mouth.*

*49. In a method of brightening teeth, the steps of:*

*(a) forming a splint to enclose one or more teeth to be brightened, said splint designed to extend onto the gingiva associated with said one or more teeth and to fit tightly to minimize saliva from impacting the enclosed teeth;*

*(b) placing a brightening solution into the splint;*

*(c) placing the splint around said one or more teeth and gingiva for a given period of time, securing the splint from said one or more teeth;*

*(d) rinsing said one or more teeth; and*

(e) *repeating steps (b) through (d) as necessary until the degree of desired brightness is achieved.*

*50. The method of claim 49 when steps (b) through (d) are repeated while the uses of the splint is sleeping at night.*

*51. The method of claim 49, wherein steps (b) through (d) are repeated during the day.*

*52. The method of claim 49, wherein steps (b) through (d) are repeated (a) while the user of the splint is asleep at night and (b) during the day.*

*53. The method of claim 49, wherein said rinsing in (d) is with a fluoride composition.*

*54. The method of brightening teeth, comprising the steps of:*

(a) *forming a substantially liquid tight splint to cover the tooth or teeth to be brightened, including at least part of the gingiva surrounding said tooth or teeth;*

(b) *placing about 1 drop per tooth or teeth to be brightened of a nascent oxygen releasing composition in said splint;*

(c) *place the splint with said composition around said tooth or teeth to be brightened and surrounding gingiva to effectively seal the splint against said gingiva; and*

(d) *reviewing the composition about every four hours during the time the splint is worn until the degree of brightness desired is achieved.*

*55. The process of brightening a tooth or teeth, comprising the steps of:*

(a) *obtaining a substantially liquid tight splint to cover the tooth or teeth to be brightened;*

(b) *placing a brightener agent at the location within said splint associated with the tooth or teeth to be brightened; and*

(c) *placing the splint containing said brightener agent around the tooth or teeth to be brightened for a number of hours a day a sufficient number of days to effect a substantial brightening of said tooth or teeth.*

*56. The method set forth in claim 55 further comprising the steps of:*

(a) *periodically removing said splint;*

(b) *adding additional brightener agent; and*

(c) *replacing said splint containing said additional brightener agent around the tooth or teeth to be brightened.*

*57. The method set forth in claim 56, further comprising the steps of:*

(a) *periodically removing said splint from said tooth or teeth;*

(b) *replacing the used brightener agent with new brightener agent; and*

(c) *reintroducing the splint with the new brightener agent with said tooth or teeth.*

*58. The process of brightening a tooth or teeth, comprising the steps of:*

(a) *obtaining a substantially liquid tight splint to cover the tooth or teeth to be brightened;*

(b) *placing a brightener agent for a number of hours each day at the location substantially within said splint associated with the tooth or teeth to be brightened; and*

(c) *placing the splint containing the brightener agent around the tooth or teeth to be brightened for a sufficient number of days to effect a substantial brightening of said tooth or teeth.*

*59. A process of brightening a stained tooth or teeth comprising the steps of:*

*obtaining a substantially liquid-tight splint to cover the tooth or teeth to be brightened;*

*placing a brightener agent at the location within said splint associated with the tooth or teeth to be brightened;*

*placing the splint containing said brightener agent around the tooth or teeth to be brightened for a number of hours;*

*periodically removing said splint and adding additional brightener agent; and*

*replacing said splint around the tooth or teeth to be brightened.*

* * * * *

UNITED STATES PATENT AND TRADEMARK OFFICE

CERTIFICATE OF CORRECTION

PATENT NO. : Re: 34,196

DATED : March 16, 1993

INVENTOR(S) : John R. Munro

It is certified that error appears in the above-indentified patent and that said Letters Patent is hereby corrected as shown below:

On the title page, item [57] Abstract, line 4, delete "comprises", insert --comprise--.

In item [56] References Cited, the requested changes are as follows:

Col. 2, line 18, delete "Baumgarttner", insert --Baumgartner--;
line 18, after "Pickett, A.B.," delete "Baumgartner", insert --Human--; and
line 35, delete "Seals", insert --Seale--.

Page 4, col. 1, line 22, delete "Gluthathione", insert --Glutathione--.

Col. 3, line 9, before "such", insert --(--; and
line 45, delete "oxygenation", insert --oxygenating--.

Col. 10, Claim 47, line 28, delete "between", insert --wherein--.

Signed and Sealed this

Seventeenth Day of May, 1994

Bruce Lehman

*Attest:*

BRUCE LEHMAN

*Attesting Officer*

*Commissioner of Patents and Trademarks*